US006831191B2

(12) United States Patent
Chaudhuri

(10) Patent No.: US 6,831,191 B2
(45) Date of Patent: Dec. 14, 2004

(54) PHOTO STABLE ORGANIC SUNSCREEN COMPOUNDS WITH ANTIOXIDANT PROPERTIES AND COMPOSITIONS OBTAINED THEREFROM

(75) Inventor: Ratan K. Chaudhuri, Lincoln Park, NJ (US)

(73) Assignee: EM Industries, Hawthorne, NY (US)

(*) Notice: Subject to any disclaimer, the term of this patent is extended or adjusted under 35 U.S.C. 154(b) by 63 days.

(21) Appl. No.: 10/022,343

(22) Filed: Dec. 20, 2001

(65) Prior Publication Data

US 2003/0157035 A1 Aug. 21, 2003

(51) Int. Cl.$^7$ ................... C07C 69/76; A61K 7/42
(52) U.S. Cl. ............ 560/105; 560/61; 424/59; 424/60; 424/400; 424/401
(58) Field of Search ............... 560/105, 61; 424/59, 424/60, 400, 401

(56) References Cited

U.S. PATENT DOCUMENTS

| | | |
|---|---|---|
| 3,256,312 A | 6/1966 | Strobel |
| 3,272,855 A | 9/1966 | Strobel |
| 3,275,520 A | 9/1966 | Strobel |
| 3,278,448 A | 10/1966 | Lauerer |
| 3,470,233 A * | 9/1969 | Bohn et al. |
| 3,535,424 A | 10/1970 | Fujimoto |
| 3,860,598 A | 1/1975 | Rosenkranz |
| 3,928,324 A | 12/1975 | Rosati |
| 3,928,429 A | 12/1975 | El-Chahawi |
| 4,284,621 A * | 8/1981 | Preuss et al. |
| 4,335,054 A | 6/1982 | Blaser |
| 4,457,911 A | 7/1984 | Conner |
| 4,504,419 A | 3/1985 | Dexter |
| 4,515,774 A | 5/1985 | Conner |
| 4,592,906 A | 6/1986 | Baker |
| 4,613,499 A | 9/1986 | Conner |
| 4,647,589 A | 3/1987 | Valone |
| 4,726,942 A | 2/1988 | Lang |
| 4,797,493 A | 1/1989 | Matsuno |
| 4,971,996 A | 11/1990 | Shiraishi et al. |
| 4,985,237 A | 1/1991 | Matsuno |
| 5,057,538 A | 10/1991 | Shiraishi et al. |
| 5,063,243 A | 11/1991 | Cho |
| 5,124,354 A | 6/1992 | Green |
| 5,175,340 A | 12/1992 | Forestier et al. |
| 5,185,370 A | 2/1993 | Backstrom et al. |
| 5,218,000 A | 6/1993 | Usherwood et al. |
| 5,283,352 A | 2/1994 | Backstrom |
| 5,326,785 A | 7/1994 | Cho et al. |
| 5,451,694 A | 9/1995 | Kuhn |
| 5,478,856 A | 12/1995 | Suzuki et al. |
| 5,514,711 A | 5/1996 | Kitano et al. |
| 5,516,839 A | 5/1996 | Ishidoya |
| 5,538,716 A | 7/1996 | Forestier |
| 5,601,811 A | 2/1997 | Gallagher et al. |
| 5,654,465 A | 8/1997 | Qian et al. |
| 5,670,140 A | 9/1997 | Deflandre |
| 5,738,842 A | 4/1998 | Raspanti et al. |
| 5,817,862 A | 10/1998 | Poetsch |
| 5,830,411 A | 11/1998 | Wang et al. |
| 5,830,441 A * | 11/1998 | Wang et al. |
| 5,888,481 A | 3/1999 | Horn et al. |
| 5,951,968 A | 9/1999 | Forestier |
| 6,066,327 A | 5/2000 | Gubernick et al. |
| 6,090,374 A | 7/2000 | Habeck |

FOREIGN PATENT DOCUMENTS

| | | |
|---|---|---|
| DE | 2816819 | 10/1979 |
| DE | 2816819 A1 * | 10/1979 |
| EP | 0631177 | 12/1994 |
| EP | 0631177 A1 * | 12/1994 |

OTHER PUBLICATIONS

CA 101:85528, Manrao et al, Evaluation of Ferulic Acid Derivatives as Antifungal Agents, Pesticides, 1984, 18 (2) 30–36.*

Wright et al, "Organic NLO Polymers," Macromolecules, 1994, 27, 3009–3015; published Dec. 1994.

International Search Report for PCT/EP02/06743.*

Green et al, Polym. Prep. (AM. Chem. Soc. Div. Polym. Chem.)1987, 28 (1), pp. 207–208, HCAPLUS document No. 106:214481.*

Shirodkar et al, Indian J. of Heterocyclic Chemistry, (1996) 6 (2) pp. 155–156, HCAPLUS document No. 126:171460.*

XP–002218456 Abstract of JP 01 013017 A (Pola Kasei Kogyo KK), Jan. 17, 1989.

XP–002218455 –Knoevenagel, E. et al., Chem. Ber., vol. 37, 1904, pp. 4476–4482.

(List continued on next page.)

Primary Examiner—Paul L Killos
Assistant Examiner—Hector M Reyes
(74) Attorney, Agent, or Firm—Millen, White, Zelano & Branigan, P.C.

(57) ABSTRACT

A compound of formula I

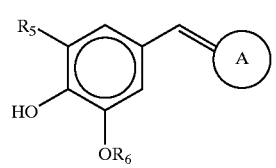

wherein

A is a moiety which provides UV absorbing activity to the compound of formula I that comprises 1 divalent group or 2 monovalent groups, with at least one group having carbonyl (C=O) functionality. $R_6$ is linear or branched $C_1$–$C_8$ alkyl and $R_5$ is a linear or branched $C_1$–$C_8$ alkyl or hydrogen. Sunscreen formulations which contain these compounds and methods for using these compounds to prepare formulations are also provided.

93 Claims, No Drawings

OTHER PUBLICATIONS

XP-000445674 –Wright M E et al., "Organic NLO Polymers 2. A Study Of Main–Chain And Guest–Host Kappa (2) NLO Polymers: NLO–Phore Structure Versus Poling" Macromolecules, American Chemical Society, Easton, U.S., vol. 27, No. 11, May 23, 1994, pp. 0024–9297.

XP-002048362 –Gazit A. et al., "Tyrphostins I: Synthesis And Biological Activity Of Protein Tyrosine Kinase Inhibitors" Journal of Medicinal Chemistry, American Chemical Society, Washington, U.S., vol. 32, No. 19, 1989, pp. 2344–2352.

XP-002193484 –Sohda T. et al., "Antiulcer activity of 5–benzylthiazolidine–2,4–dione derivatives" Chemical And Pharmaceutical Bulletin, Pharmaceutical Society of Japan, Tokyo, JP, vol. 31, No. 2, Feb. 1983 pp. 560–569.

XP001109032 Cho, H. et al., J. Med. Chem., vol. 34, 1991, pp. 1503–1506.

* cited by examiner

PHOTO STABLE ORGANIC SUNSCREEN COMPOUNDS WITH ANTIOXIDANT PROPERTIES AND COMPOSITIONS OBTAINED THEREFROM

BACKGROUND OF THE INVENTION

Topical sunscreen compositions are commonly used during outdoor work or leisure as a means for providing protection of exposed skin against acute and chronic adverse effects of solar radiation such as sunburn, cancer and photoaging. Many effective sunscreen preparations are sold commercially or are described in cosmetic or pharmaceutical literature. In general sunscreen preparations are formulated as creams, lotions or oils containing as the active agent an ultra violet radiation absorbing chemical compound. The sunscreen functions by blocking passage of ultra violet radiation thereby preventing its penetration into the skin.

According to Zecchino et al. (U.S. Pat. No. 5,008,100), sunscreen agents may be characterized in the order of decreasing effectiveness as either highly chromophoric (monomeric organic compounds and inorganic compounds such as titanium dioxide) and minimally chromophoric (polymeric organic solids).

Organic sunscreens are classified into UV-A filters, UV-B filters or broad spectrum filters (UV-A and UV-B functionality in a single molecule) depending on the type of radiation they absorb. UV-A sunscreens absorb radiation in the 320 to 400 nm regions of the ultra violet spectrum and UV-B sunscreens absorb radiation in the 290 to 320 nm regions of the ultra violet spectrum.

Broad band sunscreens (UV-A and UV-B functionality) absorb radiation in the 290 to 400 nm region of the ultra violet spectrum and have two maximums, one in the UV-B region and the other in the UV-A region.

Representative references related to UV sunscreens are:

U.S. Pat. No. 3,278,448, which discloses cinnamic acid derivatives such as 4-hydroxy, 3-5-ditertbutyl-alphacarbethoxy-cinnamic acid ether ester in column 2, line 20;

U.S. Pat. No. 3,538,226, which describes cinnamic acid alkyl ester derivatives at column 1, lines 15–31 and column 2, lines 1–12 and column 3, lines 30–55 and 60;

U.S. Pat. No. 5,175,340, which describes cinnamic acid alkyl esters having hydroxy radicals and alkoxy radicals on the phenyl ring, and U.S. Pat. No. 5,830,441, which describes UV absorbents containing a cyano or cinnamyl moiety by the generic formula at col. 2, lines 1–21.

Other references which disclose cinnamide compounds include U.S. Pat. Nos. 5,601,811, 4,335,054, 5,124,354, 5,294,643 and 5,514,711.

Unfortunately, some of the highly chromophoric monomeric organic compounds employed in sunscreen compositions are not photostable and the protection from sun damage is lost. In addition to lack of photostability of many organic sunscreens, they do not possess an antioxidant property which is essential for protecting skin or hair.

The ideal sunscreen formulation should be nontoxic and non-irritating to the skin tissue and be capable of convenient application in a uniform continuous film. The product should be chemically and physically stable so as to provide an acceptable shelf life upon storage. It is particularly desirable that the preparation should retain its protective effect over a prolonged period after application. Thus, the active agent when present on the skin must be resistant to chemical and/or photo degradation.

Techniques for stabilizing UV absorbent compositions are known. Representative disclosures in this area include U.S. Pat. Nos. 5,567,418, 5,538,716, 5,951,968 and 5,670,140.

It is desirable to provide the antioxidant and photostable sunscreen functionality in a single molecule to enhance the effectiveness of the antioxidant properties.

SUMMARY OF THE INVENTION

There is provided by the present invention compounds with sunscreen activity, i.e. they are chromophoric within the ultra violet radiation range of from 290–400 nm and they also exhibit antioxidant properties. These compounds are represented by general formula I

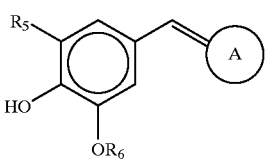

In formula I, A is a moiety which provides chromophoric properties within the UV radiation range of 290–400 nm. This moiety comprises one divalent group or two monovalent groups with at least one group having carbonyl (C=O) functionality. For formula I, each $R_6$ is independently linear or branched $C_1$–$C_8$ alkyl and $R_5$ is hydrogen or $R_6$. The one or more compounds of formula I can preferably stabilize an additional sunscreening agent against photodegradation from exposure to sunlight. Preferred compounds are of formula II below.

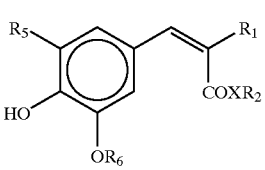

For formula II, $R_1$ is selected from the group consisting of —C(O)CH$_3$, —CO$_2$R$_3$, —C(O)NH$_2$, —C(O)N(R$_4$)$_2$, and —CN;

X is O or NH;

$R_2$ is linear or branched $C_1$ to $C_{30}$ alkyl;

$R_3$ is linear or branched $C_1$ to $C_{20}$ alkyl;

each $R_4$ is independently hydrogen or linear or branched $C_1$ to $C_8$ alkyl;

$R_5$ is linear or branched $C_1$–$C_8$ alkyl or hydrogen; and $R_6$ is linear or branched $C_1$–$C_8$ alkyl.

Included within the preferred compounds are those of formula II wherein $R_1$ is linear or branched $C_1$–$C_4$ alkyl, X is oxygen and $R_2$ is linear or branched $C_1$–$C_{12}$ alkyl. Of these compounds, those more preferred have $R_1$ as C(O)CH$_3$ or CO$_2$R$_3$ wherein $R_3$ is a linear or branched $C_1$ to $C_4$ alkyl. For compounds wherein $R_1$ is C(O)N(R$_4$)$_2$, $R_4$ is preferably hydrogen or a linear or branched $C_1$–$C_4$ alkyl.

While compounds having from $C_1$–$C_4$ alkyl groups for $R_2$ and $R_3$ are preferred, significant utility can be obtained from compounds wherein $R_2$ and $R_3$ are linear or branched $C_8$ to $C_{20}$ alkyl or $C_{12}$ to $C_{20}$ alkyl groups.

Another preferred class of compounds are those of formulae III and IV wherein $R_1$ and $R_2$ are as defined for formula I with $R_3$ being $C_1-C_8$ alkyl and $R_4$ being $C_1-C_4$ alkyl.

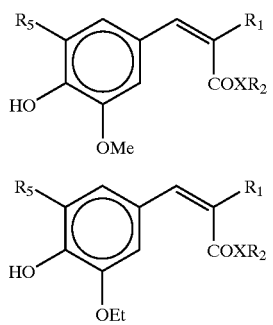

Examples of compounds consistent with Formulae III or IV include those selected from the group consisting of ethyl-alpha-cyano-3-methoxy-4-hydroxy cinnamate,
ethyl-alpha-acetyl-3-methoxy-4-hydroxy cinnamate,
iso-propyl-alpha-acetyl-3-methoxy-4-hydroxy cinnamate,
iso-amyl-alpha-acetyl-3-methoxy-4-hydroxy cinnamate,
2-ethylhexyl-alpha-acetyl-3-methoxy-4-hydroxy cinnamate,
diethyl-3-methoxy-4-hydroxy benzylidene malonate,
di-(2-ethylhexyl)-3-methoxy-4-hydroxy benzylidene malonate,
diisoamyl-3-methoxy-4-hydroxy benzylidene malonate,
didodccyl-3-methoxy-4-hydroxy benzylidene malonate,
dipalmitoyl-3-methoxy-4-hydroxy benzylidene malonate, and
di-isopropyl-3-methoxy-4-hydroxy benzylidene malonate.
di-(2-ethyhexyl)-3-methoxy-4-hydroxy-5-isopropyl-benzylidene malonate
di-isoamyl-3-methoxy-4-hydroxy-5-tert.butyl-benzylidene malonate
iso-amyl-alpha-acetyl-3-methoxy-4-hydroxy-5-isopropyl cinnamate
iso-amyl-alpha-acetyl-3-methoxy-4-hydroxy-5-tert.butyl cinnamate The present invention also provides sunscreen formulations which comprise a compound of formula I, II, III and/or IV. These sunscreen formulations are effective in absorbing illumination in the range of wavelengths of 320 nm and above. Amounts of the compounds of formula I, II, III and/or IV within such compositions typically range from 0.1 to 40 wt % based on the total weight of the sunscreen. These sunscreen formulations can contain one or more additional organic sunscreen agents for filtering UV-B or UV-A rays or they may additionally contain one or more metal oxide sunscreen agents such as titanium dioxide or zinc oxide.

These sunscreen formulations may additionally contain a carrier and at least one component selected from the group consisting of dispersing agents, preservatives, anti-foams, perfumes, oils, waxes, propellants, dyes, pigment emulsifiers, surfactants, thickeners, humectants, exfoliants and emollients. These sunscreen formulations may be in the form of a cosmetic composition with a cosmetically acceptable carrier and one or more cosmetic adjuvants. The sunscreen formulation can optionally have conventional antioxidants or other stabilizers which do not have UV absorbing characteristics.

Methods of using these sunscreen compositions and methods for improving the photostability of sunscreen formulations are also provided. The methods of using the sunscreen formulations comprise applying a sunscreen formulation which contains a compound of formula I, II, III and/or IV to a substrate. Preferred substrates are skin and hair. To improve the photostability of a sunscreen formulation, a compound of formula I, II, III and/or IV is added to the sunscreen formulation in an amount sufficient to reduce the loss of UV absorbance of the sunscreen as it is irradiated. Typical amounts fall within the range of 0.1% to 40 wt %, based on the total weight of said sunscreen formulation. More typically, the amount falls within the range of 1 wt % to 25 wt %. The amount of organic sunscreen compound of formulae I, II, III and/or IV, preferably ranges from about 3 wt % to about 15 wt % of the sunscreen formulation. Other ingredients referred to above and discussed more particularly below are generally used in an amount from about 0.1 wt % to about 10 wt % of the sunscreen formulation. The balance comprises a cosmetically or pharmaceutically acceptable carrier.

The sunscreen formulations of this invention preferably offer protection from UV radiation with wavelengths of about 290 nm to 400 nm and preferably from wavelengths in the range of about 290–370 nm. Sunscreen formulations of this invention also typically have a sunscreening protection factor (SPF) range of from about 2 to 60, with a preferred SPF range of from about 10 to about 45. The target SPF range can be achieved with a combination of both inorganic and organic chromophoric compounds. SPF is determined by techniques well known in the art, on human skin as described in the Federal Register, August 25, 1978, Vol. 43, No. 166, pages 38259–38269 (Sunscreen Drug Products for Over-The-Counter Human Use, Food and Drug Administration). SPF values can also be approximated using in-vitro models as described, for example, in J. Soc. Cosmet. Chem. 44:127–133 (May/June 1989).

The sunscreen formulations may contain dispersing agents, emulsifiers or thickening agents to assist in applying a uniform layer of the active compounds. Suitable dispersing agents for the sunscreen formulations include those useful for dispersing organic or inorganic sunscreen agents in either a water phase, oil phase, or part of an emulsion, including, for example, chitosan.

Emulsifiers may be used in the sunscreen formulations to disperse one or more of the compounds of formulae I, II, III and/or IV or other component of the sunscreen formulation. Suitable emulsifiers include conventional agents such as, for example, glycerol stearate, stearyl alcohol, cetyl alcohol, dimethicone copolyol phosphate, hexadecyl-D-glucoside, octadecyl-D-glucoside, etc.

Thickening agents may be used to increase the viscosity of the sunscreen formulations. Suitable thickening agents include carbomers, acrylate/acrylonitrile copolymers, xanthan gum and combinations of these. The carbomer thickeners include the crosslinked CARBOPOL® acrylic polymers from B.F. Goodrich. The amount of thickener within the sunscreen formulation, on a solids basis without water, may range from about 0.001 to about 5%, preferably from 0.01 to about 1% and optimally from about 0.1 to about 0.5% by weight.

Minor optional adjunct ingredients for the sunscreen formulations to be applied to skin or hair may include preservatives, waterproofing agents, fragrances, anti-foam agents, plant extracts (Aloe vera, witch hazel, cucumber, etc) opacifiers, skin conditioning agents and colorants, each in amounts effective to accomplish their respective functions.

The sunscreen formulations may optionally contain an ingredient which enhances the waterproof properties such as, compounds that form a polymeric film, such as dimethicone copolyol phosphate, dilsostearoyl trimethyolpropane siloxysilicate, chitosan, dimethicone, polyethylene, polyvinylpyrrolidone (PVP), polyvinylpyrrolidone/vinylacetate, PVP/Eiconsene copolymer and adipic acids/diethylene glycol/glycerine crosspolymer etc. Waterproofing agents may be present at levels of from about 0.01 to about 10% by weight.

The sunscreen formulations may also optionally contain one or more skin conditioning agents. These include humectants, exfoliants and emollients.

Humectants are polyhydric alcohols intended for moisturizing, reducing scaling and stimulating the removal of built scale from the skin. Typically polyhydric alcohols include polyalkylene glycols and more preferably alkylene polyols and their derivatives. Illustrative are propylene glycol, dipropylene glycol, polypropylene glycol, polyethylene glycol, sorbitol, 2-pyrrolidone-5-carboxylate, hydroxypropyl sorbitol, hexylene glycol, ethoxydiglycol 1,3-butylene glycol, 1,2,6-hexanetriol, glycerin, ethoxylated glycerin, propoxylated glycerin and mixtures thereof. Most preferably the humectant is glycerin. Amounts of humectant can range anywhere from 1 to 30%, preferably from 2 to 20% and optimally from about 5 to 10% by weight of the sunscreen composition.

The exfoliants suitable for use in the present may be selected from alpha-hydroxy carboxylic acids, beta hydroxycarboxylic acids and salts of these acids. Most preferred are glycolic, lactic and salicylic acids and their alkali, metal or ammonium salts.

Suitable emollients include those agents known for softening the skin or hair which may be selected from hydrocarbons, fatty acids, fatty alcohols and esters. Petrolatum is a common hydrocarbon type of emollient conditioning agent. Other hydrocarbons that may be employed include alkyl benzoate, mineral oil, polyolefins such as polydecene, and paraffins, such as isohexadecane. Fatty acids and alcohols typically have from about 10 to 30 carbon atoms. Illustrative are myristic, isostearic, hydroxystearic, oleic, linoleic, ricinoleic, behenic and eruicic acids and alcohols. Oily ester emollients may be those selected from one or more of the following, triglyceride esters, acetoglyceride esters, ethoxylated glycerides, alkyl esters of fatty acids, ether esters, polyhydric alcohol esters and wax esters. Additional emollients or hydrophobic agents include $C_{12}$ to $C_{15}$ alkyl benzoate, dioctyladipate, octyl stearate, octyldodecanol, hexyl laurate, octyldodecyl neopentanoate, cyclomethicone, dicapryl ether, dimethicone, phenyl trimethicone, isopropyl myristate, capriylic/capric glycerides, propylene glycol dicaprylate/dicaprate and decyl oleate.

The sunscreen formulations may optionally contain one or more inorganic sunscreen agents as discussed above including micro fine surface treated titanium dioxide and micro fine untreated and surface treated zinc oxide. Titanium dioxide in the sunscreen compositions preferably has a mean primary particle size of between 5 and 150 nm and preferably from 10 to 100 nm. Titanium dioxide may have anatase, rutile or amorphous structure. The zinc oxide in the sunscreen compositions preferably has a mean primary particle size of between 5 nm and 150 nm, preferably between 10 nm and 100 nm. Examples of modified titanium dioxide compositions include:

Eusolex® T-45D (surface treated with alumina and simethicone, 45% dispersion in isononoyl isononoate);

Eusolex®T-Aqua, (surface treated with aluminum hydroxide, 25% dispersion in water); and Eusolex® T-2000 (surface treated with alumina and simethicone), all available from MERCK KGaA.

The sunscreen formulation may also contain one or more additional monomeric organic chromophoric compounds. These can either be UV-A, UV-B or broad band filters. Examples of suitable UV-A sunscreens include benzophenone derivatives, menthyl anthranilate, butyl methoxydibenzoyl methane and benzylidene-dioxoimidazoline derivatives. Examples of suitable UV-B sunscreens include cinnamate derivatives, salicylate derivatives, para-aminobenzoic acid derivatives, camphor derivatives, phenylbenzimidazole derivatives and diphenylacrylate derivatives. Examples of suitable broad-band sunscreen include benzotriazole derivatives and triazine derivatives such as anisotriazone. Others include ethylhexyltriazone and diethylhexylbutamidotriazone.

Particularly useful organic sunscreen agents that can be introduced are Avobenzone, 2-ethylhexyl p-methoxycinnamate, 4,4'-t-butylmethoxydibenzoyl methane, 2 hydroxy-4-methoxybenzophenone, octyldimethyl p-aminobenzoic acid, 2,2-dihydroxy-4-methoxybenzophenone, ethyl-4-[bis(hydroxypropyl)] aminobenzoate, 2-ethylhexyl-2-cyano-3,3-diphenylacrylate, 2-ethylhexylsalicylate, glycerol p-aminobenzoate, 3,3,5-trimethylcyclohexylsal icylate, methylanthrani late, p-dimethylaminobenzoic acid, 2-ethylhexyl p-dimethylaminobenzoate, 2-phenylbenzimidazole-5-5-sulfonic acid, 2-(p-dimethylamino phenyl-5-sulfoniobenzoxazoic acid and mixtures thereof.

Examples of useful commercially available organic sunscreen agents that can be introduced include 2-phenylbenzimidazole-5-sulphonic acid, 2-(4-methylbenzylidene)-camphor, 4-isopropyldibenzoyl methane all of the Eusolex™ series sold by EM Industries and Merck KGaA, Darmstadt, Germany.

Although not preferred, the sunscreen formulation may contain an additional antioxidant. Examples of suitable antioxidants which provide stability include p-hydroxybenzoic acid and its derivatives (ethylisobutyl, glyceryl esters of p-hydroxybenzoic acid); salicylates (octylamyl, phenyl, benzyl menthyl, glycerol and dipropyleneglycol esters); cumarin derivatives; flavones; hydroxy or methoxy substituted benzophenones; uric or tannic acid and its derivatives; hydroquinone; and benzophenones.

In addition to providing sunscreen activity at levels which provide U.V. absorption, the compounds of Formula I can be introduced into a skin care formulation, a hair care formulation or other personal care formulations such as cosmetic formulations at levels which provide antioxidant activity. These compounds can be used with or without conventional antioxidants in personal care formulations such as hair care, skin care and cosmetic formulations.

The personal care formulations can be in the form of creams, ointments, suspensions, powders, oil, lotions, oleo alcoholic lotions, fatty gels, oleo-alcoholic gels and lotions, solid sticks, foams, emulsions, liquid dispersions, sprays and aerosols. More specific forms include: lipsticks, foundations, makeup, loose or press powder, eye blush, eye shadow and nail lacquer.

Sunscreen formulations of this invention as described in Formulations 1–9 can be prepared by conventional means.

FORMULATION 1

| Phase A | | Phase B | |
|---|---|---|---|
| Deionized water | 60.0% | Ethyl-alpha-acetyl-3,methoxy-4-hydroxy cinnamate | 8.75% |
| Disodium EDTA | .10% | Octyl salicylate | 5% |
| Glycerin | 1.5% | Aluminum stearate | 5% |
| NaCl | 3.0% | Cyclomethicone/dimethicone | 10% |
| Butylene glycol | 2.5% | Cetyl dimethicone | 1% |
| | | Cyclomethicone | 2% |
| | | ABIC-EM 97 | 1% |
| | | Fragrance | .15% |

Procedure:
Combine phase B ingredients. Stir and heat to 70–75° C. Combine Phase A ingredients. Heat while stirring to 70–75° C. Add Phase B to Phase A while stirring. Add preservative. Stir, allowing mixture to cool to room temperature.

Formulation 2: Sunscreen Oil/Water Spray Lotion

| INCI Name | Trade Name (Supplier) | % w/w |
|---|---|---|
| Phase A-1 | | |
| Di-isopropyl-3-methoxy-4-hydroxybenzylidene malonate | | 7.50 |
| Benzophenone-3 | Eusolex ® 4360 (Rona) | 2.50 |
| Dicapryl ether | Cetiol ® OE (Henkel) | 4.50 |
| Dimethicone | Dow Corning 200 ®, 50 cst (Dow) | 2.00 |
| Stearyl Alcohol | Crodacol S-70 (Croda) | 0.60 |
| PPG-2 Ceteareth-9 | Eumulgin ® L (Henkel) | 0.40 |
| Steareth-10 | Volpo 10 (Croda) | 0.50 |
| Glyceryl stearate, PEG-100 Stearate | Arlacel ® 165 (ICI) | 2.80 |
| Phase A-2 | | |
| Titanium Dioxide, Simethicone, Alumina | Eusolex ® T-2000 (Rona) | 5.00 |
| Phase B-1 | | |
| Demineralized water | | 66.10 |
| Chitosan, water | Hydagen ® CMF (Henkel) | 2.00 |
| Glycerin USP | Emery 916 (Henkel) | 2.50 |
| Dimethicone copolyol phosphate | Pecosil PS-100 (Phoenix Chemical) | 2.50 |
| Phase B-2 | | |
| Polyquaternium 37, Mineral oil, PPG-1 trideceth-6 | Salcare SC 95 (Ciba) | 0.40 |
| Phase C | | |
| Propylene Glycol, DMDM Hydantoin, Methylparaben, Propylparaben | Paragon ™ II (McIntyre) | 0.70 |
| Total | | 100.00 |

Procedure
Combine A-1; stir and heat to 60° C. until all solids are dissolved. Disperse A-2 in A-1 with agitation. Combine B-1; stir and heat to 60° C. Disperse B-2 in B-1 with agitation. Add A to B while stirring vigorously. Gently homogenize allowing mixture to cool to 40° C. Add C to A/B: gently homogenize until mixture is uniform. Stir with anchor mixer allowing mixture to reach 25° C. prior to packaging. Use a high shear pump spray device for dispensing (e.g., Eurogel pump by Seaquist Perfect)

Formulation 3: Sunscreen Cream

| INCI Name | Trade Name/Manufacturer | % w/w |
|---|---|---|
| Phase A | | |
| Deionized water | | 39.73 |
| Carbomer (2% aq. solution) | Carbopol 980/BF Goodrich | 15.00 |
| Propylene Glycol | | 5.00 |
| Methylparaben | | 0.20 |
| Propylparaben | | 0.10 |
| Triethanolamine (99%) | | 0.45 |
| Tetrasodium EDTA | | 0.02 |
| Phase B | | |
| Octyl Methoxycinnamate | Eusolex ® 2292/Rona | 5.00 |
| Benzophenone-3 | Euslex ® 44360/Rona | 3.00 |
| Di-isoamyl-3-methoxy-4-hydroxybenzylidene malonate | | 4.50 |
| Glyceryl Stearate (and) PEG-100 Stearate | Ariacel 165/ICI Surfactants | 1.00 |
| Cyclomethicone | Dow Corning 344 Fluid/Dow Corning | 5.00 |
| Glyceryl Stearate | | 4.00 |
| Stearic Acid | Emersol 132, NF/Henkel | 2.50 |
| Isostearyl Isostearate | Prisonne ISIS 2039/Unichema | 10.00 |
| Hydrogenated Castor Oil | Castorwax/CasChem | 2.00 |
| $C_{12-15}$ Alcohols Benzoate | Finsolv TN/Finetex | 2.50 |
| Total | | 100.00 |

Procedure
Add Phase A ingredients to main vessel under impeller agitation. Heat phase A to 75–80° C. Combine Phase B ingredients; heat and mix to 85° C. Slowly add Phase B to batch; mix for 15 minutes at 85° C. Remove from heat; switch to paddle mixing and cool to room temperature.

Formulation 4: Water/Oil Broad Spectrum Sunscreen Lotion

| INCI Name | Trade Name/Manufacturer | % w/w |
|---|---|---|
| Phase A-1 | | |
| Octyl Methoxycinnamate | Eusolex ® 2292/Rona | 7.50 |
| Iso-amyl-alpha-acetyl-3-methoxy-4-hydroxy-cinnamate | | 5.00 |
| Octyl Stearate | Cetiol 868/Henkel | 2.00 |
| Dicapryl Ether | Cetiol OE/Henkel | 3.00 |
| Cyclomethicone | Dow Corning 345 Fluid/Dow Corning | 4.00 |
| Dimethicone | DC 200 fluid 50 cST/Dow Corning | 2.00 |
| PEG-30 Dipolyhydroxystearate | Ariacel P135/ICI | 1.30 |
| Laurylmethicone copolyol | Dow Corning formulation Aid 5200/Dow | 2.30 |
| Behenamidopropyl dimethylainine Behenate | Catemol 220-B/Phoenix Chemical | 0.50 |
| Phase A-2 | | |
| Titanium Dioxide (and) Alumina (and) Simethicone | Eusolex T-2000/Rona | 8.00 |
| Deionized Water | | 61.00 qs |
| Propylene Glycol | | 2.00 |
| Sodium Chloride | | 0.80 |
| Phase C | | |
| DMDM Hydantoin, Methylparaben, Propylparaben | Paragon II/McIntyre | 0.60 |
| Total | | 100.00 |

Procedure

Combine A-1; stir and heat to 55–60° C. until all solids are dissolved. Disperse A-1 in A-1 by propeller agitation. Combine B; stir and heat to 50–55° C. Slowly add B to A while stirring vigorously. Add C to A/B; gently homogenize until mixture is uniform. Stir with anchor mixer allowing mixture to cool to room temperature.

Formulation 5: UVA/UVB Sun Protection Cream with Avobenzone

| INCI Name | Trade Name/Manufacturer | % w/w |
|---|---|---|
| Phase A-1 | | |
| Water (demineralized) | | 67.80 |
| Disodium EDTA | | 0.05 |
| Propylene glycol | | 3.00 |
| Methylparaben | | 0.15 |
| Phase A-2 | | |
| Carbomer | Carbopol Ultrez 10/BF Goodrich | 0.20 |
| Phase B | | |
| Isopropyl Myristate | | 2.00 |
| Cetyl Alcohol, Glyceryl Stearate, PEG-75 Stearate, Ceteth 20, Steareth 20 | Emulium Delta/Gattefosse | 4.00 |
| Diethyl-3-methoxy-4-hydroxybenzylidene malonate | | 3.50 |
| Homomethyl salicylate | Eusolex ® HMS/Rona | 7.00 |
| Octyl salicylate | Eusolex ® OS/Rona | 7.00 |
| Butyl methoxydibenzoyl-methane | Eusolex ® 9020/Rona | 3.00 |
| Dimethicone | Dow Corning Fluid 200, 100 sct/Dow | 1.00 |
| C30–38 Olefin/Isopropyl Maleate/MA Copolymer | Performa V 1608/New Phase Technologies | 1.00 |
| Phase C | | |
| Triethanolamine (99%) | | 0.30 |
| Phase D | | |
| preservatives | | q.s. |
| Total | | 100.00 |

Procedure

Combine A-1; heat to 50° C. while stirring until methylparaben is dissolved. Disperse A-2 in A-1 with a sifter. Heat A to 65° C. Combine B: heat to 65–70° C. while stirring until solids are dissolved. Add B to A. Homogenize Add C at 55–60° C. Continue to homogenize allowing mixture to cool to 40–45° C. Add D; stir with propeller mixer until uniform. Adjust pH with TEA to 6.5–7.0

Formulation 6: Oil/Water Sunscreen Lotion

| INCI Name | Trade Name/Manufacturer | % w/w |
|---|---|---|
| Phase A | | |
| Diisoamyl-3-methoxy-4-hydroxybenzylidene malonate | | 3.00 |
| Isopropyl Myristate | Emerest 2314/Henkel | 4.00 |
| C12–15 Alkyl Benzoate | Finsolv TN/Finetex | 4.00 |
| Cetyl Alcohol | Crodacol C-70/Croda | 1.50 |
| Steareth-2 | Bnj 72/ICI Surfactants | 2.00 |
| Steareth-21 | Bnj 721/ICI Surfactants | 2.50 |
| Dimethicone | Dow Corning Fluid 200, 100 sct/Dow | 0.50 |
| Phase B | | |
| Deionized/Water | | 81.07 |
| Alkyl Acrylates | Carbopol ETD 2020/BF Goodrich | 0.20 |
| Phase C | | |
| Triethanolamine (99%) | TEA 99%/Union Carbide | 0.23 |
| Phase D | | |
| Phenoxyethanol (and) isopropylparaben (and)isobutylparaben (and) but paraben | Liquapar PE/Sutton | 1.00. |
| Total | | 100.00 |

Procedure

Prepare Phase B by dispersing Carbopol in water. Heat the dispersion to 70–75° C. Combine Phase A ingredients. Stir and heat to 70–75° C. Add Phase B to Phase A while stirring. Add Phase C. Homogenize until mixture cools to 45–40° C. Add Phase D. Stir allowing mixture to cool to room temperature.

Formulation 7: Oil/Water Sunscreen Lotion

| INCI Name | Trade Name/Manufacturer | % w/w |
|---|---|---|
| Phase A | | |
| Avobenzone | Eusolex 9020/Rona | 3.00 |
| Diisoamyl-3-methoxy-4-hydroxybenzylidene malonate | | 3.00 |
| Isopropyl Myristate | Emerest 2314/Henkel | 4.00 |
| C12–15 Alkyl Benzoate | Finsolv TN/Finetex | 4.00 |
| Cetyl Alcohol | Crodacol C-70/Croda | 1.50 |
| Steareth-2 | Bnj 72/ICI Surfactants | 2.00 |
| Steareth-2 | Bnj 721/ICI Surfactants | 2.50 |
| Dimethicone | Dow Corning Fluid 200, 100 sct/Dow | 0.50 |
| Phase B | | |
| Deionized Water | | 78.07 |
| Acrylayes/C10–30 Alkyl Acrylates Crosspolymer | Carbopol ETD 2020/BF Goodrich | 0.20 |
| Phase C | | |
| Triethanolamine (99%) | TEA 99%/Union Carbide | 0.23 |
| Phase D | | |
| Phenoxyethanol (and) isopropylparaben (and)isobutylparaben (and) butylparaben | Liquapar PE/Sutton | 1.00 |
| Total | | 100.00 |

Procedure

Preapare Phase B by dispersing Carbopol in water. Heat the dispersion to 70–75° C. Combine Phase A ingredients. Stir and heat to 70–75° C. Add Phase B to Phase A while stirring. Add Phase C. Homogenize until mixture cools to 45–40° C. Add Phase D. Stir allowing mixture to cool to room temperature.

| Formulation 8: Oil/Water Sunscreen Lotion | | |
| --- | --- | --- |
| INCI Name | Trade Name/Manufacturer | % w/w |
| Phase A | | |
| Avobenzone | Eusolex 9020/Rona | 3.00 |
| Disoamyl-3-methoxy-4-hydroxy-5-isopropyl benzylidene malonate | | 3.00 |
| Isopropyl Myristate | Emerest 2314/Henkel | 4.00 |
| C12–15 Alkyl Benzoate | Finsolv TN/Finetex | 4.00 |
| Cetyl Alcohol | Crodacol C-70/Croda | 1.50 |
| Steareth-2 | Bnj 72/ICI Surfactants | 2.00 |
| Steareth-21 | Bnj 721/ICI Surfactants | 2.50 |
| Dimethicone | Dow Corning Fluid 200, 100 sct/Dow | 0.50 |
| Phase B | | |
| Deionized Water | | 78.07 |
| Acrylayes/C10–30 Alkyl Acrylates Crosspolymer | Carbopol ETD 2020/BF Goodrich | 0.20 |
| Phase C | | |
| Triethanolamine (99%) | TEA 99%/Union Carbide | 0.23 |
| Phase D | | |
| Phenoxyethanol (and) isopropylparaben (and)isobutylparaben (and) butylparaben | Liquapar PE/Sutton | 1.00 |
| Total | | 100.00 |

Procedure

Preapare Phase B by dispersing Carbopol in water. Heat the dispersion to 70–75° C. Combine Phase A ingredients. Stir and heat to 70–75° C. Add Phase B to Phase A while stirring. Add Phase C. Homogenize until mixture cools to 45–40° C. Add Phase D. Stir allowing mixture to cool to room temperature.

| Formulation 9: Oil/Water Sunscreen Lotion | | |
| --- | --- | --- |
| INCI Name | Trade Name/Manufacturer | % w/w |
| Phase A | | |
| Avobenzone | Eusolex 9020/Rona | 3.00 |
| Isoamyl-alpha-acetyl-3-methoxy-4-hydroxy-5-isopropyl cinnamate | | 3.00 |
| Isopropyl Myristate | Emerest 2314/Henkel | 4.00 |
| C12—15 Alkyl Benzoate | Finsolv TN/Finetex | 4.00 |
| Cetyl Alcohol | Crodacol C-70/Croda | 1.50 |
| Steareth-2 | Bnj 72/ICI Surfactants | 2.00 |
| Steareth-21 | Bnj 721/ICI Surfactants | 2.50 |
| Dimethicone | Dow Corning Fluid 200, 100 sct/Dow | 0.50 |
| Phase B | | |
| Deionized Water | | 78.07 |
| Acrylayes/C10–30 Alkyl Acrylates Crosspolymer | Carbopol ETD 2020/BF Goodrich | 0.20 |
| Phase C | | |
| Triethanolamine (99%) | TEA 99%/Union Carbide | 0.23 |
| Phase D | | |
| Phenoxyethanol (and) isopropylparaben (and)isobutylparaben (and) butylparaben | Liquapar PE/Sutton | 1.00 |
| Total | | 100.00 |

Procedure

Preapare Phase B by dispersing Carbopol in water. Heat the dispersion to 70–75° C. Combine Phase A ingredients. Stir and heat to 70–75° C. Add Phase B to Phase A while stirring. Add Phase C. Homogenize until mixture cools to 45–40° C. Add Phase D. Stir allowing mixture to cool to room temperature.

Methods of preparation of two compounds of the invention are illustrated below.

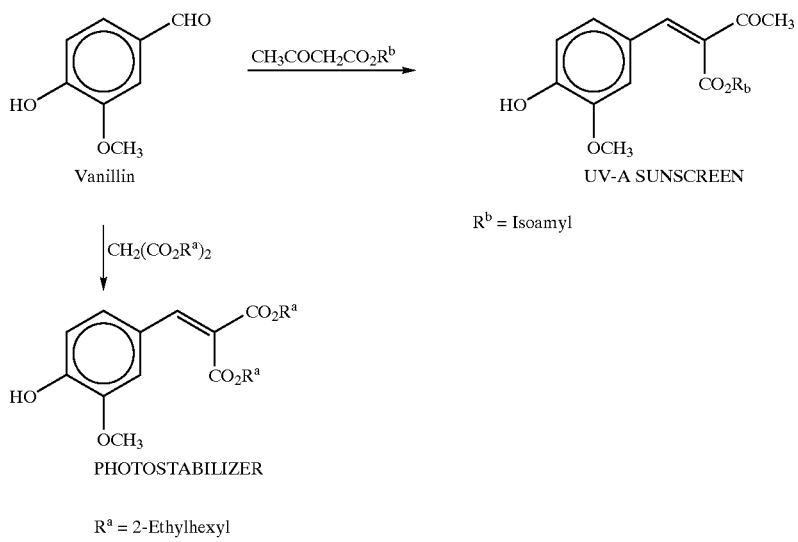

$R^b$ = Isoamyl $R^a$ = 2-Ethylhexyl

The resultant sunscreens have been found to have an SPF of approximately 14.

The entire disclosure of all applications, patents and publications, cited above are hereby incorporated by reference.

EXAMPLES

Example I

Ethyl-alpha-cyano-3-methoxy-4-hydroxy cinnamate Condensation of vanillin with ethyl cyanoacetate in the presence of piperidine—acetic acid and benzene as the reaction medium at reflux temperature under continuous azeotropic water removal yields the title product. The reaction takes about 1.5 hours for completion. The yield obtained is typically 95%.

Example II

Diethyl-3-methoxy-4-hydroxy benzylidene malonate Condensation of 3-methoxy-4-hydroxy benzaldehyde (vanillin) with diethyl malonate in the presence of piperidine—acetic acid and benzene as the reaction medium at reflux temperature under continuous azeotropic water removal yields the title product. The reaction takes about 6.5 hours for completion.

Example III

Ethyl-alpha-acetyl-3-methoxy-4-hydroxy-cinnamate Condensation of 3-methoxy-4-hydroxy benzaldehyde (vanillin) with ethyl acetoacetate in the presence of piperidine—acetic acid and benzene as the reaction medium at reflux temperature yields the title product. The reaction takes about 3.5 hours for completion.

Example IV

Di-(2-Ethylhexyl)-3-methoxy-4-hydroxy benzylidene malonate Transesterification of diethyl malonate using 2-ethylhexyl alcohol in neat condition at 140–155° C. for 2 hours under nitrogen blanketing in the presence of sulfuric acid and after work up, followed by high vacuum distillation, yields di-6-ethylhexyl malonate. Condensation of 3-methoxy-4-bydroxy benzaldehyde (vanillin) with di-2-ethylhexyl malonate in the presence of piperidine—acetic acid and benzene as the reaction medium at reflux temperature under continuous azeotropic water removal yields di-2-ethylhexyl-3-methoxy-4-hydroxy benzylidene malonate. The reaction takes about nine hours for completion. The yield typically obtained is 91%.

Example V

Di-isoamyl-3-methoxy-4-hydroxy benzylidene malonate Example IV is repeated, except in the condensation step, di-2-ethyhexyl malonate is replaced with di-isoamyl malonate. The yield typically obtained is over 90%.

Example VI

Di-isopropyl-3-ethoxy-4-hydroxy benzyl idene malonate Example IV is repeated, except in the condensation step, di-2-ethyhexyl malonate is replaced with di-isopropyl malonate. The yield typically obtained is over 90%.

Example VII

Di-dodecyl-3-methoxy-4-hydroxy benzylidene malonate Example IV is repeated, except in the condensation step, di-2-ethyhexyl malonate is replaced with di-dodecyl malonate. The yield typically obtained is over 90%.

Example VIII

Iso-propyl-alpha-acetyl-3-methoxy-4-hydroxy-cinnamate Example III is repeated, except in the condensation step, ethyl acetoacetate is replaced with iso-propyl acetoacetate. The yield of the desired product is 88%.

Example IX

Iso-butyl-alpha-acetyl-3-methoxy-4-hydroxy-cinnamate Example III is repeated, except in the condensation step, ethylacetoacetate is replaced with iso-butyl-acetoacetate. The yield of the desired product is 89%.

Example X

Iso-amyl-alpha-acetyl-3-methoxy-4-hydroxy-cinnamate Example III is repeated, except in the condensation step, ethylacetoacetate is replaced with iso-amyl acetoacetate. The yield of the desired product is 89%.

Example XI

Disoamyl-3-methoxy-4-hydroxy-5-isopropyl benzylidene malonate Condensation of 3-methoxy-4-hydroxy-5-isopropyl benzaldehyde with di-isoamyl malonate in the presence of piperidine-acetic acid and benzene as the reaction medium at reflux temperature under continuous azeotropic water removal yields the title product. The reaction takes about 3 hours for completion. The yield obtained is typically 90–95%.

Example XII

Isoamyl-alpha-acetyl-3-methoxy-4-hydroxy-5-isopropyl-cinnamate Condensation of 3-methoxy-4-hydroxy-5-isopropyl benzaldehyde with isoamyl acetoacetate in the presence of piperidine-acetic acid and benzene as the reaction medium at reflux temperature under continuous azeotropic water removal yields the title product. The reaction takes about 4 hrs for completion. The yield obtained is typically 90–95%.

Stabilizing Activity

Sunscreen compounds selected from the list below were evaluated for their photostability profile and photostabilization of Avobenzone following the protocol described below. Results are summarized in Table 1.

Compounds are illuminated in a solar simulator incorporating a 1 kw Xe arc lamp, optical bench and illumination chamber. The entire output of the illumination system is focused onto the face of a 1 centimeter Cuvette (an area of 4 cm$^2$) that contains the dilute samples of a compound of Formula I. The samples experience roughly 250 J/cm$^2$ of radiation between 290 and 400 nm over a period of two hours. The solutions contain between 0.0056 mg/ml and 2.5 mg/ml.

Photostability of the individual compounds is determined by differential UV-absorption spectra before and after illumination. % Loss of absorption, hence the loss of individual compound, is calculated from the reduction in optical density after illumination. Likewise, stabilization of Avobenzone in the presence of individual compounds of this invention was also calculated.

TABLE 1

Results of Photostability & their Stabilization of Selected Compounds of this Invention

| Compound | $\lambda_{max}$, nm (Ethanol) | Photo-stability % Loss in 2 hrs | Stabilization of Avobenzone[2] % Loss of Avobenzone in 2 hrs |
|---|---|---|---|
| Di-(2-ethylhexyl)-3-methoxy-4-hydroxy benzylidene malonate | 332 | 1 | 4.5 |
| Di-isoamyl-3-methoxy-4-hydroxy benzylidene malonate | 333 | 3.2 | 3.8 |
| Isoamyl-alpha-acetyl-3-methoxy-4-hydroxy cinnamate | 339 | 4.1 | insignificant |
| Di-(2-ethylhexyl)-3-methoxy-4-hydroxy-5-isopropyl-benzylidene malonate | 334 | 2 | 2.5 |
| Isoamyl-alpha-acetyl-3-methoxy-4-hydroxy-5-isopropyl cinnamate | 341 | 3.2 | insignificant |
| Avobenzone | 358 | 37 | |
| Octocrylene (control) | 303 | 2.8 | 1.5 |

[1]Solvent used 70% ethanol/30% water; solar simulator; about 250 J/cm$^2$
[2]Product/Avobenzone (1:1, w/w); % Loss of Avobenzone by HPLC DPPH Test Method A DPPH concentrate (2.5×) of 25 mg of 1,1-Diphenyl-2-Picyrl-Hydrazyl ACS# 1898-66-4 (Sigma #D-9132, lot 99H3601) dissolved in 250 mL ethanol (USP), is prepared fresh on the measurement date. A DPPH working solution is then prepared by diluting 100 mL of this concentrate to a final volume of 250 mL (100 μM/mL). A blank 13×100 mm borosilicate glass screw top tube of ethanol (USP) is used to zero the spectrometer (Milton Roy, Spectronic 20+) at 517 nm and a control tube of DPPH working solution is measured under identical conditions, and taken as 0% activity. Aliquots of the 0.25% & 0.5% (RT & 45° C.) test solution are added to tubes followed by the rapid addition of 4 mL DPPH working solution then rapidly capped and mixed. After 20 minutes, the absorbance of each sample is read at 517 nm.

The percent reducing activity (% RA) is calculated using the following equation:

$$\% \text{ Reduction Activity} = 100 \frac{A(0) - A(20)}{A(0)}$$

Where A(0) is the absorbance value of the DPPH working solution at 517 nm zeroed against an ethanol blank and A(20) is the absorbance at 517 nm, 20 minutes after combining the antioxidant with the DPPH working solution.

The concentration of antioxidant (mg/ml) in the final assay mixture is calculated based on the dilution of respective aliquots of each compound in the final assay volume and % RA tabulated and plotted as percent activity at each concentration in the dilution series.

Antioxidant Property

The antioxidant activity of selected compounds of this invention was determined from their reducing activity of a DPPH radical. Results of selected compounds from this invention are summarized in Table 2.

TABLE 2

Antioxidant Activity of Selected Compounds of this Invention

| Compounds | % Reducing Activity of DPPH Radical at 30 μg/ml | μg/ml Needed to Reduce 50% of DDPPH radical (Lc$_{50}$) |
|---|---|---|
| Di-(2-ethylhexyl)-3-methoxy-4-hydroxy benzylidene malonate | 7.4 | 188 |
| Di-isoamyl-3-methoxy-4-hydroxy benzylidene malonate | 9.5 | 172 |
| Isoamyl-alpha-acetyl-3-methoxy-4-hydroxy cinnamate | 22 | 72 |
| Di-(2-ethylhexyl)-3-methoxy-4-hydroxy-5-isopropyl-benzylidene malonate | 11.2 | 161 |
| Isoamyl-alpha-acetyl-3-methoxy-4-hydroxy-5-isopropyl cinnamate | 28 | 68 |
| Tinogard | | 46 |

In order to boost antioxidant activity of the compounds of the present invention, other antioxidants can be combined. Some examples are those antioxidants mentioned above and Tocopherols, tocopherylacetate, Ascorbic acid, Emblica antioxidants, Proanthocyanidins (from pine bark, grape seed extract, and the like) green tea polyphenols, rosemary antioxidants, gallic acid, ellagic acid, butylhydroxy toluene (BHT), butylhydroxy anisole (BHA) and the like.

Photostability

The photostability of selected compounds (see Table 1) was tested according to the procedures below.

A solar simulator used for illumination of the samples in the experiments is constructed incorporating a 1 kw Xe arc lamp, optical bench and sample illumination chamber. The lamp output is filtered through a water filter with a course window to remove most of the infrared radiation and optical filters to remove wavelengths below 290 nm. The output of the illumination system is focused onto the face of a 1 cm quartz Cuvette that is thermally equilibrated with a constant temperature water bath at 25° C. A magnetic stir is mounted under the Cuvette so that the samples could be stirred while being illuminated. An electric shutter is controlled by a dark room timer to provide precise control of illumination times. The solar simulator is constructed to provide illumination that closely matches terrestrial sunlight. The solar simulator delivers roughly 250 J/cm$^2$ over a 2-hour period of illumination in a 290–490 nm range. This irradiance is determined using two nitrobenzaldehyde chemical actinometry. The irradiance is much higher than other solar simulator systems which typically illuminate a large area in order to illuminate many samples simultaneously rather than being focused down to a very small area.

Each sunscreen compound is dissolved in 70% ethanol/30% water and the UV visible absorption spectrum measured with a Shimadza UV 2101 -double beam spectrophotometer using the solvent as reference. A control solution of Octocrylene is prepared and the UV-visible absorption spectrum measured. Each solution is then illuminated for two hours in the solar simulator. After illumination, the absorption spectrum is again measured for each solution.

As Table 1 illustrates, the tested compounds were found to be photostable after two hours of illumination in a Xe-arc solar simulator. This data shows compounds of this invention have comparable photostabilities to Octocrylene under the experimental conditions employed.

The UV-spectral study of the present inventive compounds shows that they have broad absorption bands that extend across the UV region. They exhibit lower molar absorption than Avobenzone but have much better photostability than Avobenzone (see Table 1).

Stabilizing Activity

The stabilizing activity of selected compounds (see Table 1) toward Avobenzone was tested and compared with a conventional product according to the procedures below.

Individual solutions of selected sunscreen compounds (see Table 1) with Avobenzone were as follows. Each sunscreen compound was dissolved in 50% ethanol/50% $H_2O$ solution containing roughly an equal molar amount of Avobenzone. A similar solution containing Di-2-ethylhexyl-2,6-napthalene dicarboxylic acid (DENDA) and Avobenzone was also prepared. Each solution was then illuminated in the solar simulator as configured above for the photostability tests and aliquots of each solution were removed at 30-minute time intervals. These aliquots were injected into an HPLC and the loss of Avobenzone was followed with illumination time. The high performance liquid chromatograph (HPLC) used for all experiments reported therein incorporated a Spectra-Physics model P-200 pump with an Applied Biosystems model 785A UV-Visible detector with a Rheodyne manual injector incorporating a 50 ml sample loop and a 150×4.6 mm reversed-phase $C_{18}$ column (Alltech). All analyses were carried out under isocratic elution conditions using $CH_3OH/H_2O$ mixtures for the mobile phase at a flow rate of 1 $H_2O$ ml per minute. It was necessary to employ HPLC separation of Avobenzone from each of the sunscreen compounds to quantify Avobenzone due to the absorption spectra overlap with some of these compounds.

The loss of Avobenzone when illuminated alone in solution rapidly exhibited a loss of 37% in 2 hours in the solar simulator (Table 1).

The preceding examples can be repeated with similar success by substituting the generically or specifically described reactants and/or operating conditions of this invention for those used in the examples. From the foregoing description, one skilled in the art can easily ascertain the essential characteristics of this invention, and without departing from the spirit and scope thereof, can make various changes and modifications of the invention to adapt it to various usages and conditions.

What is claimed is:

1. A compound of formula II

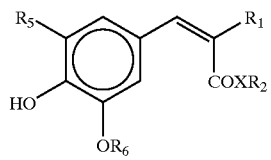

II wherein
$R_1$ is selected from the group consisting of —C(O)CH$_3$, —CO$_2R_3$, —C(O)NH$_2$, —C(O)N(R$_4$)$_2$;
X is O or NH;
$R_2$ is linear or branched $C_3$ to $C_{30}$ alkyl;
$R_3$ is linear or branched $C_3$ to $C_{20}$ alkyl; and
each $R_4$ is independently hydrogen, or linear or branched $C_1$ to $C_8$ alkyl;
$R_5$ is linear or branched $C_1$–$C_8$ alkyl or hydrogen, and $R_6$ is $C_1$ to $C_8$ alkyl.

2. A compound of claim 1 wherein X is oxygen and $R_2$ is linear or branched $C_1$ to $C_4$ alkyl.

3. A compound of claim 2 wherein $R_1$ is $CO_2R_3$ and, $R_3$ is linear or branched $C_3$ to $C_8$ alkyl.

4. A compound of claim 2 wherein $R_1$ is C(O)CH$_3$.

5. A compound of claim 2 wherein $R_1$ is —C(O)N(R$_4$)$_2$, and at least one $R_4$ is hydrogen and the other is hydrogen or linear or branched $C_1$ to $C_4$ alkyl.

6. A compound of claim 2 wherein $R_1$ is —C(O)N(R$_4$)$_2$, and each $R_4$ is independently linear or branched $C_1$ to $C_4$ alkyl.

7. A compound of claim 1 wherein $R_6$ is $C_1$–$C_4$ alkyl, $R_1$ is —CO$_2R_3$, and at least one of $R_2$ and $R_3$ is linear or branched $C_8$ to $C_{20}$ alkyl.

8. A compound of claim 7 wherein $R_2$ and $R_3$ are each linear or branched $C_8$–$C_{12}$ alkyl.

9. A compound of claim 7 wherein at least one of $R_2$ and $R_3$ is linear or branched $C_{12}$ to $C_{20}$ alkyl.

10. A compound as in claim 1 wherein $R_6$ is methyl or ethyl.

11. A compound of one of the formulae

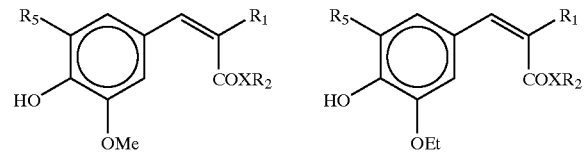

wherein
$R_1$ is selected from the group consisting —C(O)CH$_3$, —CO$_2$ (C$_1$–C$_8$alkyl), —C(O)NH$_2$, —C(O)N(C$_1$–C$_4$ alkyl)$_2$, and —CN;
X is O or NH; and
$R_2$ is $C_2$–$C_{12}$ alkyl, and
$R_5$ is $C_1$–$C_8$ linear or branched alkyl.

12. A compound of claim 11 wherein X is oxygen and $R_2$ is linear or branched $C_1$ to $C_4$ alkyl.

13. A compound of claim 11 wherein $R_1$ is —CO$_2C_8H_{18}$.

14. A compound selected from the group consisting of
iso-propyl-alpha-acetyl-3-methoxy-4-hydroxy cinnamate,
iso-amyl-alpha-acetyl-3-methoxy-4-hydroxy cinnamate,
2-ethylhexyl-alpha-acetyl-3-methoxy-4-hydroxy cinnamate,
di-(2-ethylhexyl)-3-methoxy-4-hydroxy benzylidene malonate,
diisoamyl-3-methoxy-4-hydroxy benzylidene malonate,
dipalmitoyl-3-methoxy-4-hydroxy benzylidene malonate,
di-dodecyl-3-methoxy-4-hydroxy benzylidene malonate,
di-isopropyl-3-methoxy-4-hydroxy benzylidene malonate,
di-(2-ethyhexyl)-3-methoxy-4-hydroxy-5-isopropyl-benzylidene malonate,
di-isoamyl-3-methoxy-4-hydroxy-5-tert.butyl-benzylidene malonate,
iso-amyl-alpha-acetyl-3-methoxy-4-hydroxy-5-isopropyl cinnamate, and
iso-amyl-alpha-acetyl-3-methoxy-4-hydroxy-5-tert.butyl cinnamate.

15. A sunscreen formulation comprising a compound of claim 1 in an amount effective to absorb illumination in a range above 320 nm wavelength.

16. A sunscreen formulation comprising a compound of claim 1 in an amount effective to absorb illumination in a range of 290 to 400 nm wavelength.

17. A sunscreen formulation as in claim 15, which comprises from 0.1 to 40 wt. % of a compound of formula II.

18. A sunscreen formulation as in claim 15 comprising an additional organic sunscreen agent for filtering UV-B, UV-A rays or both.

19. A sunscreen formulation as in claim 17 wherein the compound of formula II stabilizes the additional sunscreen agent against degradation from exposure to light.

20. A sunscreen formulation as in claim 17, which additionally comprises an inorganic metal oxide sunscreen agent.

21. A personal care formulation that comprises a compound of claim 1 in an amount effective to absorb illumination in a range above 320 nm wavelength, a cosmetically acceptable carrier and at least one cosmetic adjuvant selected from the group consisting of preservatives, antifoams, perfumes, oils, waxes, propellants, dyes, pigments, waterproofing agents, emulsifiers, surfactants, thickeners, humectants, exfoliants and emollients.

22. A personal care formulation as in claim 21 which is in a form selected from the group consisting of creams, ointment, suspensions, powders, oily lotions, oleo-alcoholic lotions, fatty gels, oleo-alcoholic gels, solid sticks, foams, emulsions, liquid dispersions, sprays and aerosols.

23. A sunscreen formulation as in claim 18, which is free of photostabilizers other than compounds of formula II, which is present in an amount within the range of 0.1% to 40 wt % of said sunscreen formulation.

24. A method of protecting a substrate from UV radiation which comprises applying a sunscreen formulation of claim 15 to said substrate.

25. A method as of protecting a substrate of skin or hair from UV radiation which comprises applying a personal care formulation of claim 21 to a substrate of skin or hair.

26. A method of improving the photostability of a sunscreen formulation said method comprising adding a compound of formula II of claim 1 to said sunscreen formulation in an amount sufficient to improve the photostability of said sunscreen agent.

27. A method as in claim 26 wherein the amount of compound of formula II added to the sunscreen formulation falls within the range of 0.1% to 40 wt % of said sunscreen formulation.

28. A method as in claim 25 wherein the personal care formulation additionally comprises an antioxidant selected from the group consisting of tocopherols, tocopherylacetate, Ascorbic acid, Emblica antioxidants, Proanthocyanidins, Rosemary antioxidants, green tea polyphenols, gallic acid, ellagic acid, butylhydroxy toluene and butylhydroxy anisole.

29. A personal care formulation comprising at least one compound of claim 1 and an antioxidant other than a compound of formula II.

30. A personal care formulation as in claim 29 wherein the antioxidant is selected from the group consisting of Tocopherols, tocopherylacetate, Ascorbic acid, Emblica antioxidants, Proanthocyanidins, Rosemary antioxidants, green tea polyphenols, gallic acid, ellagic acid, butylhydroxy toluene and butylhydroxy anisole.

31. A personal care formulation which comprises a compound of claim 1 in an amount effective to protect formulation ingredients from oxidation.

32. A personal care formulation as in claim 31, which is in the form of lipsticks, foundation, make-up, loose or press powder, eye blush, eye shadows or nail lacquer.

33. A compound of the formula below

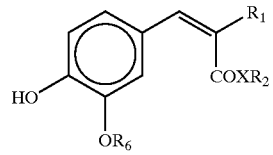

wherein
R$_1$ is selected from the group consisting of —C(O)CH$_3$, —CO$_2$R$_3$, —C(O)NH$_2$, and —C(O)N(R$_4$)$_2$,
X is O or NH;
R$_2$ is linear or branched C$_3$ to C$_{30}$ alkyl;
R$_3$ is linear or branched C$_1$ to C$_{20}$ alkyl;
each R$_4$ is independently hydrogen, or linear or branched C$_1$ to C$_8$ alkyl;
and R$_6$ is C$_1$ to C$_8$ alkyl;
subject to at least one of provisos a)–e):
 a) R$_1$ is —CO$_2$R$_3$ and R$_3$ is linear or branched C$_3$ to C$_{20}$ alkyl,
 b) R$_1$ is —C(O)N(R$_4$)$_2$ and at least one R$_4$ is linear or branched C$_1$ to C$_8$ alkyl,
 c) R$_2$ is linear or branched C$_3$ to C$_{30}$ alkyl
 d) X is NH or
 e) R$_6$ is C$_2$ to C$_8$ alkyl.

34. A compound of claim 33 wherein R$_1$ is —CO$_2$R$_3$ and R$_3$ is linear or branched C$_8$ to C$_{20}$ alkyl.

35. A compound of claim 33 wherein R$_1$ is —C(O)N(R$_4$)$_2$ and at least one R$_4$ is linear or branched C$_1$ to C$_8$ alkyl.

36. A compound of claim 33 wherein R$_2$ is linear or branched C$_8$ to C$_{20}$ alkyl.

37. A compound of claim 33 wherein X is NH.

38. A sunscreen formulation comprising a compound of claim 14 in an amount effective to absorb illumination in a range above 320 nm wavelength.

39. A sunscreen formulation comprising a compound of claim 33 in an amount effective to absorb illumination in a range above 320 nm wavelength.

40. A sunscreen formulation as in claim 38 comprising an additional organic sunscreen agent for filtering UV-B, UV-A rays or both.

41. A sunscreen formulation as in claim 39 comprising an additional organic sunscreen agent for filtering UV-B, UV-A rays or both.

42. A personal care formulation that comprises a compound of claim 14 in an amount effective to absorb illumination in a range above 320 nm wavelength, a cosmetically acceptable carrier and at least one cosmetic adjuvant selected from the group consisting of preservatives, antifoams, perfumes, oils, waxes, propellants, dyes, pigments, waterproofing agents, emulsifiers, surfactants, thickeners, humectants, exfoliants and emollients.

43. A personal care formulation that comprises a compound of claim 33 in an amount effective to absorb illumination in a range above 320 nm wavelength, a cosmetically acceptable carrier and at least one cosmetic adjuvant selected from the group consisting of preservatives, antifoams, perfumes, oils, waxes, propellants, dyes, pigments, waterproofing agents, emulsifiers, surfactants, thickeners, humectants, exfoliants and emollients.

44. A method of protecting a substrate from UV radiation which comprises applying a sunscreen formulation of claim 38 to said substrate.

45. A method of protecting a substrate from UV radiation which comprises applying a sunscreen formulation of claim 39 to said substrate.

46. A method of improving the photostability of a sunscreen formulation said method comprising adding a compound of claim 14 to said sunscreen formulation in an amount sufficient to improve the photostability of said sunscreen agent.

47. A method of improving the photostability of a sunscreen formulation said method comprising adding a compound of claim 33 to said sunscreen formulation in an amount sufficient to improve the photostability of said sunscreen agent.

48. A personal care formulation which comprises a compound of claim 1 in an amount effective to protect formulation ingredients from oxidation.

49. A personal care formulation which comprises a compound of claim 33 in an amount effective to protect formulation ingredients from oxidation.

50. A compound of formula II

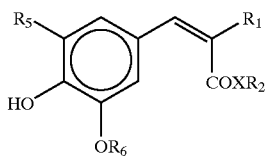

wherein
$R_1$ is selected from the group consisting of —C(O)CH$_3$, —CO$_2$R$_3$, and —C(O)NH$_2$, —C(O)N(R$_4$)$_2$;
X is O or NH;
$R_2$ is linear or branched $C_3$ to $C_{30}$ alkyl;
$R_3$ is linear or branched $C_1$ to $C_{20}$ alkyl; and
each $R_4$ is independently hydrogen, or linear or branched $C_1$ to $C_8$ alkyl;
$R_5$ is linear or branched $C_1$–$C_8$ alkyl or hydrogen, and $R_6$ is $C_1$ to $C_8$ alkyl.

51. A compound of claim 50 wherein $R_6$ is $C_1$–$C_8$ alkyl, X is oxygen and $R_2$ is linear or branched $C_3$ to $C_4$ alkyl.

52. A compound of claim 50 wherein $R_1$ is CO$_2$R$_3$ and, $R_3$ is linear or branched $C_1$ to $C_8$ alkyl.

53. A compound as in claim 50 wherein $R_6$ is methyl or ethyl.

54. A compound of formula II

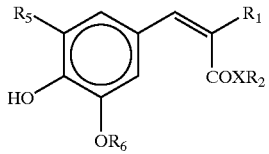

wherein
$R_1$ is selected from the group consisting of —C(O)CH$_3$, —CO$_2$R$_3$, —C(O)NH$_2$, —C(O)N(R$_4$)$_2$, and —CN;
X is O or NH;
$R_2$ is linear or branched $C_1$ to $C_{30}$ alkyl;
$R_3$ is linear or branched $C_1$ to $C_{20}$ alkyl; and
each $R_4$ is independently hydrogen, or linear or branched $C_1$ to $C_8$ alkyl;
$R_5$ is linear or branched $C_1$–$C_8$ alkyl, and $R_6$ is $C_2$ to $C_8$ alkyl.

55. A compound of claim 54 wherein $R_6$ is $C_1$–$C_8$ alkyl, X is oxygen and $R_2$ is linear or branched $C_1$ to $C_4$ alkyl.

56. A compound of claim 54 wherein $R_1$ is CO$_2$R$_3$ and, $R_3$ is linear or branched $C_1$ to $C_8$ alkyl.

57. A compound of claim 54 wherein $R_1$ is C(O)CH$_3$.

58. A compound of claim 54 wherein $R_1$ is —C(O)N(R$_4$)$_2$, and at least one $R_4$ is hydrogen and the other is hydrogen or linear or branched $C_1$ to $C_4$ alkyl.

59. A compound of claim 54 wherein $R_1$ is —C(O)N(R$_4$)$_2$, and each $R_4$ is independently linear or branched $C_1$ to $C_4$ alkyl.

60. A compound as is claim 54 wherein $R_6$ is methyl or ethyl.

61. A compound according to claim 1, wherein $R_5$ is isopropyl or tert-butyl.

62. A compound according to claim 21, wherein $R_5$ is isopropyl or tert-butyl.

63. A compound according to claim 50, wherein $R_5$ is isopropyl or tert-butyl.

64. A compound according to claim 54, wherein $R_5$ is isopropyl or tert-butyl.

65. A sunscreen formulation comprising a compound of claim 50 in an amount effective to absorb illumination in a range above 320 nm wavelength.

66. A sunscreen formulation comprising a compound of claim 50 in an amount effective to absorb illumination in a range of 290 to 400 nm wavelength.

67. A sunscreen formulation as in claim 66 comprising an additional organic sunscreen agent for filtering UV-B, UV-A rays or both.

68. A sunscreen formulation as in claim 66, which additionally comprises an inorganic metal oxide sunscreen agent.

69. A personal care formulation that comprises a compound of claim 50 in an amount effective to absorb illumination in a range above 320 nm wavelength, a cosmetically acceptable carrier and at least one cosmetic adjuvant selected from the group consisting of preservatives, antifoams, perfumes, oils, waxes, propellants, dyes, pigments, waterproofing agents, emulsifiers, surfactants, thickeners, humectants, exfoliants and emollients.

70. A personal care formulation as in claim 69 which is in a form selected from the group consisting of creams, ointment, suspensions, powders, oily lotions, oleo-alcoholic lotions, fatty gels, oleo-alcoholic gels, solid sticks, foams, emulsions, liquid dispersions, sprays and aerosols.

71. A sunscreen formulation as in claim 66, which is free of photostabilizers other than compounds of formula II, which is present in an amount within the range of 0.1% to 40 wt % of said sunscreen formulation.

72. A personal care formulation comprising at least one compound of claim 50 and an antioxidant other than a compound of formula II.

73. A sunscreen formulation comprising a compound of claim 54 in an amount effective to absorb illumination in a range above 320 nm wavelength.

74. A sunscreen formulation comprising a compound of claim 54 in an amount effective to absorb illumination in a range of 290 to 400 nm wavelength.

75. A sunscreen formulation as in claim 73 comprising an additional organic sunscreen agent for filtering UV-B, UV-A rays or both.

76. A sunscreen formulation as in claim 73, which additionally comprises an inorganic metal oxide sunscreen agent.

77. A personal care formulation that comprises a compound of claim 54 in an amount effective to absorb illumination in a range above 320 nm wavelength, a cosmetically acceptable carrier and at least one cosmetic adjuvant selected from the group consisting of preservatives, antifoams, perfumes, oils, waxes, propellants, dyes, pigments, waterproofing agents, emulsifiers, surfactants, thickeners, humectants, exfoliants and emollients.

78. A personal care formulation as in claim 77 which is in a form selected from the group consisting of creams, ointment, suspensions, powders, oily lotions, oleo-alcoholic lotions, fatty gels, oleo-alcoholic gels, solid sticks, foams, emulsions, liquid dispersions, sprays and aerosols.

79. A sunscreen formulation as in claim 73, which is free of photostabilizers other than compounds of formula II, which is present in an amount within the range of 0.1% to 40 wt % of said sunscreen formulation.

80. A personal care formulation comprising at least one compound of claim 54 and an antioxidant other than a compound of formula II.

81. A sunscreen formulation comprising a compound of claim 14 in an amount effective to absorb illumination in a range of 290 to 400 nm wavelength.

82. A sunscreen formulation as in claim 38 comprising an additional organic sunscreen agent for filtering UV-B, UV-A rays or both.

83. A sunscreen formulation as in claim 38, which additionally comprises an inorganic metal oxide sunscreen agent.

84. A personal care formulation as in claim 42 which is in a form selected from the group consisting of creams, ointment, suspensions, powders, oily lotions, oleo-alcoholic lotions, fatty gels, oleo-alcoholic gels, solid sticks, foams, emulsions, liquid dispersions, sprays and aerosols.

85. A sunscreen formulation as in claim 38, which is free of photostabilizers other than compounds of formula II, which is present in an amount within the range of 0.1% to 40 wt % of said sunscreen formulation.

86. A personal care formulation comprising at least one compound of claim 14 and an antioxidant other than a compound of formula II.

87. A personal care formulation which comprises a compound of claim 14 in an amount effective to protect formulation ingredients from oxidation.

88. A personal care formulation which comprises a compound of claim 50 in an amount effective to protect formulation ingredients from oxidation.

89. A personal care formulation which comprises a compound of claim 54 in an amount effective to protect formulation ingredients from oxidation.

90. A compound of formula II

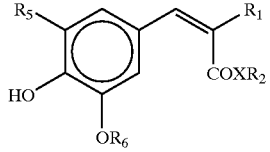

wherein
$R_1$ is selected from the group consisting of —$CO_2R_3$, and —$C(O)NH_2$, —$C(O)N(R_4)_2$;
X is O or NH;
$R_2$ is linear or branched $C_1$ to $C_{30}$ alkyl;
$R_3$ is linear or branched $C_3$ to $C_{20}$ alkyl; and
each $R_4$ is independently hydrogen, or linear or branched $C_1$ to $C_8$ alkyl;
$R_5$ is linear or branched $C_1$–$C_8$ alkyl or hyrdrogen,
and $R_6$ is $C_1$ to $C_8$ alkyl.

91. A compound of one of the formulae

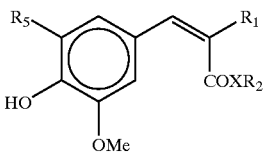 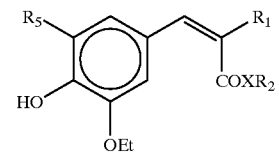

wherein
$R_1$ is selected from the group consisting —$C(O)CH_3$, —$CO_2$ ($C_1$–$C_8$), —$C(O)NH_2$, —$C(O)N(C_1$–$C_4$ alkyl$)_2$, and —CN;
X is O or NH; and
$R_2$ is $C_1$–$C_{12}$ alkyl, and
$R_5$ is $C_2$–$C_8$ linear or branched alkyl.

92. A compound of the formula below

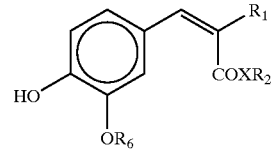

wherein
$R_1$ is selected from the group consisting of —$CO_2R_3$, —$C(O)NH_2$, and —$C(O)N(R_4)_2$,
X is O or NH;
$R_2$ is linear or branched $C_1$ to $C_{30}$ alkyl;
$R_3$ is linear or branched $C_1$ to $C_{20}$ alkyl;
each $R_4$ is independently hydrogen, or linear or branched $C_1$ to $C_8$ alkyl;
and $R_6$ is $C_1$ to $C_8$ alkyl;
subject to at least one of provisos a)–e):
a) $R_1$ is —$CO_2R_3$ and $R_3$ is linear or branched $C_3$ to $C_{20}$ alkyl,
b) $R_1$ is —$C(O)N(R_4)_2$ and at least one $R_4$ is linear or branched $C_1$ to $C_8$ alkyl,
c) $R_2$ is linear or branched $C_3$ to $C_{30}$ alkyl
d) X is NH or
e) $R_6$ is $C_2$ to $C_8$ alkyl.

93. A compound of formula II

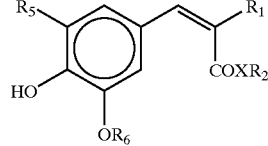

II wherein
$R_1$ is selected from the group consisting of —$C(O)CH_3$, —$CO_2R_3$, —$C(O)NH_2$, —$C(O)N(R_4)_2$, and —CN;
X is O or NH;
$R_2$ is linear or branched $C_3$ to $C_{30}$ alkyl;
$R_3$ is linear or branched $C_1$ to $C_{20}$ alkyl; and
each $R_4$ is independently hydrogen, or linear or branched $C_1$ to $C_8$ alkyl;
$R_5$ is linear or branched $C_1$–$C_8$ alkyl,
and $R_6$ is $C_1$ to $C_8$ alkyl.

* * * * *

UNITED STATES PATENT AND TRADEMARK OFFICE
CERTIFICATE OF CORRECTION

PATENT NO.        : 6,831,191 B2
APPLICATION NO. : 10/444744
DATED             : December 14, 2004
INVENTOR(S)      : Ratan K. Chaudhuri Page 1 of 1

It is certified that error appears in the above-identified patent and that said Letters Patent is hereby corrected as shown below:

Column 18, line 30, reads "$C_8$alkyl" should read -- $C_8$ alkyl --
Column 22, line 8, reads "as is claim" should read -- as in claim --
Column 23, line 66, reads "hyrdrogen" should read -- hydrogen --
Column 24, line 12, reads "($C_1$-$C_8$) should read -- ($C_1$-$C_8$ alkyl) --

Signed and Sealed this

Fifteenth Day of August, 2006

JON W. DUDAS
*Director of the United States Patent and Trademark Office*

UNITED STATES PATENT AND TRADEMARK OFFICE
CERTIFICATE OF CORRECTION

PATENT NO. : 6,831,191 B2
APPLICATION NO. : 10/022343
DATED : December 14, 2004
INVENTOR(S) : Ratan K. Chaudhuri It is certified that error appears in the above-identified patent and that said Letters Patent is hereby corrected as shown below:

Column 18, line 30, reads "$C_8$alkyl" should read -- $C_8$ alkyl --
Column 22, line 8, reads "as is claim" should read -- as in claim --
Column 23, line 66, reads "hyrdrogen" should read -- hydrogen --
Column 24, line 12, reads "$(C_1-C_8)$ should read -- $(C_1-C_8$ alkyl) --

This certificate supersedes Certificate of Correction issued on August 15, 2006.

Signed and Sealed this

Nineteenth Day of September, 2006

JON W. DUDAS
*Director of the United States Patent and Trademark Office*